(12) United States Patent
Dudzik et al.

(10) Patent No.: US 7,125,585 B2
(45) Date of Patent: Oct. 24, 2006

(54) SILOXANE COMPOUNDS AND THEIR USE AS HOMOGENIZER IN RELEASE AGENTS WITH MATTING EFFECT FOR PRODUCING MOLDINGS FROM PLASTICS WITH MATT SURFACES

(75) Inventors: Horst Dudzik, Essen (DE); Wilfried Knott, Essen (DE); Helmut Lammerting, Witten (DE)

(73) Assignee: Goldschmidt GmbH, Essen (DE)

( * ) Notice: Subject to any disclaimer, the term of this patent is extended or adjusted under 35 U.S.C. 154(b) by 353 days.

(21) Appl. No.: 10/670,055

(22) Filed: Sep. 24, 2003

(65) Prior Publication Data
US 2004/0062734 A1    Apr. 1, 2004

(30) Foreign Application Priority Data
Sep. 26, 2002    (EP) ................... 02021506

(51) Int. Cl.
B05D 1/12    (2006.01)
(52) U.S. Cl. ............... 427/427.4; 427/427.5; 428/423.1; 428/447
(58) Field of Classification Search .............. None
See application file for complete search history.

(56) References Cited

U.S. PATENT DOCUMENTS 6,015,920 A * 1/2000 Schilling et al. ............ 556/479
6,221,485 B1 * 4/2001 Sanchez et al. ............. 428/352
2001/0025080 A1 * 9/2001 Kobayashi et al. ......... 524/588

FOREIGN PATENT DOCUMENTS

DE    38 21 908 A1    1/1990
DE    42 38 290 C1    12/1993

* cited by examiner

*Primary Examiner*—Marc S. Zimmer
(74) *Attorney, Agent, or Firm*—Frommer Lawrence & Haug LLP

(57) ABSTRACT

The invention relates to siloxane compounds of the general formula (I)

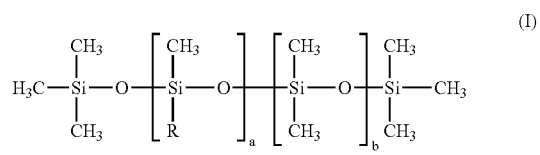

where
R is an unbranched or branched hydrocarbon radical having from 16 to 50 carbon atoms;
a is a value from 0.8 to 1.5;
b is a value from a to 3, and to their use as homogenizer in release agents with matting effect.

11 Claims, No Drawings

SILOXANE COMPOUNDS AND THEIR USE AS HOMOGENIZER IN RELEASE AGENTS WITH MATTING EFFECT FOR PRODUCING MOLDINGS FROM PLASTICS WITH MATT SURFACES

RELATED APPLICATIONS

This application claims priority to European application Serial No. 02021506.7, filed Sep. 26, 2002, herein incorporated by reference.

DESCRIPTION OF THE RELATED ART

1. Field of the Invention

The invention relates to novel siloxane compounds and to their use as homogenizer in release agents with matting effect for molding to produce moldings from plastics, in particular from polyurethanes.

2. Description of Related Art

When moldings are produced from plastics, in particular from polyurethanes, it is usual to provide the molds with a release agent prior to introduction of the plastic, in order to make demolding easier. The release agents are intended to be effective in small amounts which ensure satisfactory demolding of the molding but which, after demolding, have no adverse effect on further processing and further operations, for example painting or adhesive bonding.

Specifically in the case of moldings which have to have a very high-quality surface, e.g. shoe soles and heels or plastics moldings in vehicle construction, these moldings produced in the molds have to have the best possible capability for release from the molds, with no damage to the surfaces or impairment of their quality.

Release substances used in the prior art are mainly silicones, or else waxes, paraffins, esters and salts of fatty acids, and fluorinated hydrocarbons.

To obtain a uniform thin film on the mold wall, it is advantageous to use minimum-viscosity release agent preparations with high wetting ability. This generally requires the use of solvent-containing preparations, whereupon the solvents are intended to evaporate from the mostly heated surface of the mold wall, and to leave behind a thin release agent film.

The release action of these formulations, which mainly comprise silicones, is generally sufficient to meet industrial requirements. However, the resultant moldings have unsatisfactory surface quality and often have excessively glossy surfaces.

However, for reasons related to applications technology and in particular to fashion, there is an increasing demand for matt surfaces rather than glossy surfaces.

A reduction in the degree of gloss, i.e. the range from matt surfaces to non-reflective appearance, is obtained by structuring the surfaces of the moldings. For this, matting agents must additionally be introduced into the release agents.

The usual matting agents used are particles whose size is from 1 to 15 micrometers, but not above 50 micrometers, and which have comparatively narrow particle size distribution, the reason being that larger particles give surface irregularities.

Examples of the matting agents used in the prior art are porous phyllosilicates (Syloid® grades from Grace), which have average particle sizes preferably from 1 to 10 micrometers; synthetic polymer particles, such as polyamide particles (Orgasol® grades from Atochem), which have particle sizes from 1 to 10 micrometers; but preference is given to the use of waxes, such as paraffin waxes, in particular polyethylene waxes with molecular weights of from about 800 to 1200 daltons and with melting points of from about 90 to 100° C., and also other waxy polymers.

These are usually dispersed in isoparaffins/aliphatic hydrocarbons so that they are present in fine-particle form and can be admixed with the abovementioned release agent preparation. Once these formulations have been applied by spraying onto the mold wall using conventional spraying equipment, mostly with the use of a carrier gas, such as air or inert gas, they do not form a homogeneous film but have non-uniform distribution, a direct consequence of this therefore being that inhomogeneities and varying degrees of matting are produced on the surfaces of the moldings, instead of uniform matting.

Another adverse effect observed from this uneven distribution has been a reduction in the release effect.

OBJECTS OF THE INVENTION

It is an object, inter alia, of the present invention, therefore, to find matting agents which do not reduce the release effect of the release agent formulations and which produce a uniform matt surface on the surfaces of the plastics moldings, in particular polyurethane moldings.

This object is achieved through novel oligomeric siloxane compounds which contain long-chain hydrocarbon radicals and which are added to the silicone/wax dispersions. These and other objects are apparent from the following description of the invention.

SUMMARY OF THE INVENTION

The invention therefore provides for siloxane compounds of the general general formula (I)

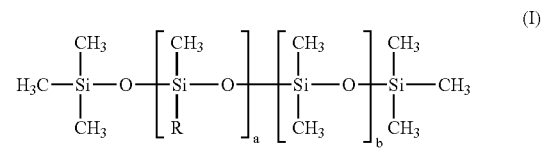

where
R is an unbranched or branched hydrocarbon radical having from 16 to 50 carbon atoms;
a is a value from 0.8 to 1.5, preferably from 1.0 to 1.3;
b is a value from 0.8 to 3.

The invention further provides for the use of the siloxane compounds of the general formula (I)

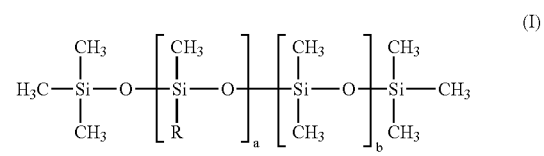

where
R, a and b are as defined above,
as homogenizer in release agents with a matting effect for molding to produce moldings from plastics, in particular from polyurethanes.

DISCUSSION OF THE INVENTION

The inventive compounds of the general formula (I) may be prepared by reacting hydrosiloxanes of the general formula (Ia)

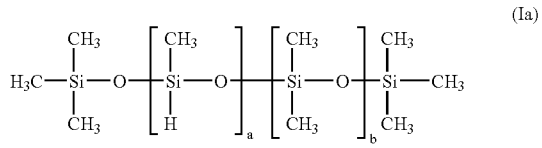

where
a and b are as defined above, with α-olefins of the general formula (Ib): $H_2C=CH-R^a$
where
$R^a$ is an unbranched or branched hydrocarbon radical having from 16 to 50 carbon atoms, by the well-known hydrosilation process.

According to the invention, preference is given to the commercially available mixtures of these α-olefins with melting points in the range from about 50 to about 80° C., preferably from about 70 to about 80° C.

The starting materials of which concomitant use is made in preparing the release agents of the invention with matting effect may be the known release agent formulations which comprise silicone oils and, as matting agent, waxes, silicates, or Aerosils.

An example is provided by the known high-performance silicone-based formulations, such as the release agents known from DE-A 38 21 908, which comprise from 60 to 70% parts by weight polydimethyltetracyclosiloxane (octamethylcyclotetrasiloxane), from 20 to 30% parts by weight of polydimethylpentacyclosiloxane (decamethylcyclopentasiloxane), and from 5 to 10 parts by weight of silicone resins, and also from 5 to 10% parts by weight of silicone oils.

Another example is provided by the formulations known from DE-C 42 38 290, composed of from 0.1 to 5% by weight of a polysiloxane containing γ-aminopropyl groups, where the γ-aminopropyl groups may have substitution on the nitrogen atom, from 4.0 to 60% by weight of a polysiloxane of the formula (II)

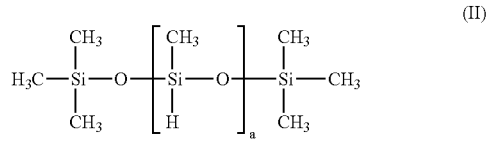

where
a is a number from 2 to 6, and the polysiloxane is free from compounds in which a<2, and comprises not more than 2% by weight of compounds in which a>6, and from 35.0 to 95.9% by weight of a volatile solvent or solvent mixture.

The materials added as homogenizer to these release agents with matting effect are the inventive compounds of the general formula (I), their amounts being from about 0.5 to about 5% by weight, preferably from about 1.5 to about 4% by weight, based on the entire formulation.

When the formulation of the invention is used, it is first applied by spraying onto the mold wall, using conventional spray equipment, mostly with use of a carrier gas, such as air or inert gas. The molds have generally retained heat from their prior use, and the solvent therefore evaporates rapidly. The release agent and the matting agent are then present in a thin homogeneous layer on the wall of the mold. The mold is then locked. The thermoplastic or the chemically curing plastic is charged to the mold. The molding is removed from the mold after solidification and/or cooling.

EXAMPLES

The following non-limiting examples illustrate the invention.

Tests for Performance Properties:

Examples of Preparation of the Substances of the Invention

Example 1

In a 250 ml four-neck flask equipped with stirrer having a precision glass gland and with dropping funnel, high-performance condenser, and nitrogen supply, 170.7 g of a $C_{30+}$-α-olefin mixture (olefin having a chain length of more than 30 atoms) with an average molar mass of 529 g/mol were heated to 90° C., with stirring, together with 170 g of an isoparaffin (Cobersol B 56), and treated with 10 ppm of Pt in the form of bis(μ-chloro)cyclohexeneplatinum(II) chloride as catalyst. 60 g of a pendant hydrosiloxane of the structure $MD_{1.8}D_{1.2}{}^HM$ (SiH content: 3.26 eq/kg) were metered in by way of the dropping funnel in a period of 20 minutes. The SiC linking reaction, which proceeded slowly, takes a total of 6.5 hours, and further catalysis (10 ppm of Pt in the form of bis(μ-chloro)cyclohexeneplatinum(II) chloride) was required 3 hours after the start of the dropwise addition. At the end of the reaction, the SiH conversion indicated by SiH determination via gas volume (decomposition of a weighed specimen with sodium butoxide, liberating hydrogen) was 98.6%.

After cooling of the reaction mixture, the alkylsiloxane was isolated as an almost colorless wax.

Example 2

Using a method similar to that of example 1, 141.4 g of a $C_{30+}$-α-olefin mixture (olefin having a chain length of more than 30 atoms) with a molar mass of 529 g/mol were heated to 90° C., with stirring, together with 141 g of an isoparaffin (Cobersol B 56), and treated with 10 ppm of Pt in the form of bis(μ-chloro)cyclohexeneplatinum(II) chloride as catalyst. 60 g of a pendant hydrosiloxane of the structure $MD_2D^HM$ (SiH content: 2.70 eq/kg) were added dropwise within a period of 20 minutes. The SiH conversion achieved in this very slow reaction during the course of 7 hours and with addition of further platinum catalyst (10 ppm) was 96%, determined via gas volume.

The alkylsiloxane obtained is colorless and has a waxy consistency.

Example 3

In an apparatus as described in Example 1, a solution composed of 185.9 g of a $C_{30+}$-α-olefin mixture (olefin having a chain length of more than 30 atoms) with a molar mass of 529 g/mol was heated to 90° C., with stirring, together with 186 g of an isoparaffin (Cobersol B 56), and treated with 10 ppm of Pt in the form of bis(μ-chloro) cyclohexeneplatinum(II) chloride as catalyst. 60 g of a pendant hydrosiloxane (structural type: MD1, 7DH1, 3M, SiH content: 3.55 eq/kg) were added dropwise during the course of 20 minutes. With further catalysis (fresh addition of 10 ppm of Pt catalyst after 3 hours), the SiH conversion achieved by the mixture after a total of 6.5 hours was >98%, determined via gas volume.

A colorless wax was obtained.

Example 4

In a 250 ml four-neck flask equipped with stirrer having a precision glass gland and with dropping funnel, high-performance condenser, and nitrogen supply, 129.1 g of an α-olefin cut having from 24 to 28 carbon atoms with an average molar mass of 400 g/mol were heated to 90° C., with stirring, together with 129 g of an isoparaffin (Cobersol B 56), and treated with 10 ppm of Pt in the form of bis(μ-chloro)cyclohexeneplatinum(II) chloride as catalyst. 60 g of the pendant hydrosiloxane used in example 1 (SiH content: 3.26 eq/kg, structural type: MD1, 8DH1, 2M) were added dropwise over the course of 20 min. SiH determination via gas volume showed the SiC linking reaction to be 98% concluded after about 6.5 hours, with further catalysis during that period.

A colorless silicone wax was obtained.

Examples for Testing the Performance Properties of the Substances of the Invention:

To test these substances of the invention as in examples 1 to 4, solvent-containing release agent dispersions were prepared, these comprising the following constituents:
a) each substance of the invention as in examples 1 to 4
b) dimethylpolysiloxane, viscosity 100 mPas
c) paraffin wax, freezing point 91° C.
d) aliphatic hydrocarbon, boiling range from 170 to 190° C.
e) decamethylcyclopentasiloxane To test the release agent dispersions, a polyurethane foam of density 0.9 kg/dm$^2$ is produced. For this, use is made of a test mold composed of aluminum and capable of being locked using a separate cover and screw clamps. The mold is preheated to a temperature of 50° C. The release agent preparation to be tested is sprayed, using a pneumatic atomizer gun, onto the inner surface of the test mold and of the cover, so as to produce a coherent film.

The Polyol/isocyanate Mixture is Prepared as Follows:

171 g of a foamable polyester polyol component are mixed for 7 sec with 192 g of an isocyanate component composed of 4,4-diisocyanatodiphenylmethane, through vigorous stirring, using a laboratory stirrer at 2500 rpm. The reaction mixture, which is still a liquid, is poured into the previously prepared aluminum mold, and the cover is put in place and locked, using screw clamps. After a holding time of 4 min., the cover is removed. The tensile forces needed here are measured by using a spring balance, and the appearance of the parts is moreover assessed in terms of matting effect and uniformity of the surfaces. Using each release agent preparation, 10 successive demoldings are carried out, and a statistical average is generated from the release forces determined.

The release agent dispersions are first shown in table 1 below, and the testing of these dispersions is shown in table 2 (from 1 to 6 being inventive, and from 7 to 9 being non-inventive).

TABLE 1

Release agent preparations (amounts given in % by weight)

| Example | HC | DmPS | PW | Silicone oil Parts | Inventive copolymer a | b | R |
|---|---|---|---|---|---|---|---|
| 1 | 48 | 45 | 2.5 | 2.5 | 2.0 | 1.2 | 1.8 | 30 |
| 2 | 48 | 45 | 2.5 | 2.5 | 2.0 | 1.2 | 1.8 | 24–28 |
| 3 | 48 | 45 | 2.5 | 2.5 | 2.0 | 1.0 | 2.0 | 30 |
| 4 | 48 | 45 | 2.5 | 2.5 | 2.0 | 1.3 | 1.7 | 30 |
| 5 | 48 | 45 | 1.5 | 3.5 | 2.0 | 1.2 | 1.8 | 30 |
| 6 | 48 | 45 | 3.5 | 1.5 | 2.0 | 1.2 | 1.8 | 30 |
| 7 | 48 | 45 | 2.5 | 2.5 | — | — | — | — |
| 8 | 48 | 45 | 1.5 | 3.5 | — | — | — | — |
| 9 | 48 | 45 | 3.5 | 1.5 | — | — | — | — |

HC = aliphatic hydrocarbon
DmPS = decamethylcyclopentasiloxane
PW = paraffin wax Assessment of release effect as in table 2:

| | |
|---|---|
| from 1 to 2 N/dm$^2$ | very good |
| from 3 to 4 N/dm$^2$ | good |
| from 5 to 6 N/dm$^2$ | moderate |
| from 7 to 8 N/dm$^2$ | adequate |
| >8 N/dm$^2$ | inadequate |

The examples for release agent preparations 1 to 6 are inventive, and examples 7 to 9 are non-inventive

TABLE 2

Testing of release agent preparations:

| Example | Optical assessment of surfaces | Assessment of release effect |
|---|---|---|
| 1 | matt, uniform | very good |
| 2 | matt, uniform | very good |
| 3 | matt, uniform | very good |
| 4 | matt, uniform | good |
| 5 | satin finish, uniform | very good |
| 6 | very matt, uniform | good |
| 7 | matt with glossy areas, non-uniform | moderate |
| 8 | matt with glossy areas, non-uniform | good |
| 9 | matt with glossy areas, non-uniform | moderate |

It is apparent that the moldings which were demolded using the preparations of the invention have very matt surfaces with uniform and satisfactory optical properties. The prior-art formulations of 7 to 9 exhibited non-uniform optical properties, and were partly glossy and partly matt, and therefore unacceptable. It has therefore been demonstrated that concomitant use of the compounds of the invention gives a considerable desired improvement in the surface quality of moldings, because it is now possible to produce moldings without additional post-treatment.

At the same time, therefore, it has been shown that the substances of the invention have a dispersing effect in formulations which comprise waxy polymers and silicone polymers.

The above description is intended to be illustrative and not limiting. Vaious changes or modifications in the embodiments described herein may occur to those skilled in the art. These can be made without departing from the scope and spirit of the invention.

What is claimed is:

1. A release agent formulation with a matting effect which comprises at least one silicone oil, at least one matting agent and at least one siloxane compound wherein the siloxane compound has the general formula (I)

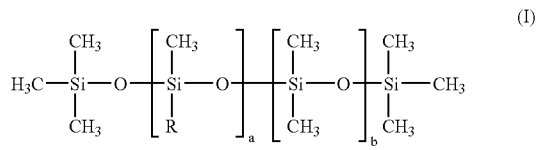

where

R is an unbranched or branched hydrocarbon radical having from 16 to 50 carbon atoms;

a is a value from 0.8 to 1.5;

b is a value from 0.8 to 3.

2. The release agent formulation of claim 1, wherein a has a value of from about 1.0 to about 1.3.

3. The release agent formulation of claim 1, wherein R is a hydrocarbon radical whose average number of carbon atoms is 30.

4. The release agent formulation according to claim 1 wherein the siloxane compound is present in an amount from about 0.5 to about 5% by weight, based upon the total weight of the formulation.

5. The release agent formulation according to claim 4, wherein the siloxane is present in an amount from about 1.5 to about 4% by weight, based upon the total weight of the formulation.

6. The release agent formulation according to claim 1 wherein the matting agent is a wax, silicate or synthetic polymer particles.

7. A method for preparing matted, molded plastics using a mold which comprises spraying onto a side of the mold the release agent formulation according to claim 1 and adding the plastic to the mold.

8. The method according to claim 7, wherein the plastic is a polyurethane foam.

9. A method for preparing matted, molded plastics using a mold which comprises spraying onto a side of the mold a release agent formulation according to claim 1.

10. A matted, molded plastic obtained by the process according to claim 9.

11. The matted, molded plastic according to claim 10, wherein the plastic is polyurethane.

* * * * *